（12）United States Patent
Joshi et al.

(10) Patent No.: US 10,561,758 B2
(45) Date of Patent: Feb. 18, 2020

(54) NONLEAKING VOLATILE SUBSTANCE DELIVERY SYSTEM

(71) Applicant: Microlin, LLC, Salt Lake City, UT (US)

(72) Inventors: Ashok V Joshi, Salt Lake City, UT (US); David J Erekson, Tooele, UT (US)

(73) Assignee: Microlin LLC, Salt Lake City, UT (US)

( * ) Notice: Subject to any disclaimer, the term of this patent is extended or adjusted under 35 U.S.C. 154(b) by 61 days.

(21) Appl. No.: 15/960,501

(22) Filed: Apr. 23, 2018

(65) Prior Publication Data

US 2018/0236120 A1    Aug. 23, 2018

Related U.S. Application Data

(63) Continuation-in-part of application No. 15/396,759, filed on Jan. 2, 2017, now Pat. No. 10,183,091, which is a continuation of application No. 14/632,970, filed on Feb. 26, 2015, now Pat. No. 9,533,066, and a continuation-in-part of application No. 14/537,691, filed on Nov. 10, 2014, now Pat. No. 9,623,135.

(60) Provisional application No. 61/944,698, filed on Feb. 26, 2014, provisional application No. 61/902,031, filed on Nov. 8, 2013.

(51) Int. Cl.
*A61L 9/12* (2006.01)
*B01F 3/04* (2006.01)

(52) U.S. Cl.
CPC ............. *A61L 9/12* (2013.01); *A61L 9/127* (2013.01); *B01F 3/04* (2013.01)

(58) Field of Classification Search
CPC .................................. B01F 3/04; A61L 9/12
USPC .................................................. 261/83, 107
See application file for complete search history.

(56) References Cited

U.S. PATENT DOCUMENTS

| 4,623,337 A | 11/1986 | Maurice |
| 5,483,953 A * | 1/1996 | Cooper ................. A61M 11/06 128/200.14 |
| 5,879,095 A | 3/1999 | Gueret |
| 2005/0036823 A1 | 2/2005 | Butcher et al. |

(Continued)

OTHER PUBLICATIONS

Copenheaver et al. "International Search Report" for PCT Application No. PCT/US2015/017837, dated Jun. 3, 2015, 2 pages.

(Continued)

*Primary Examiner* — Robert A Hopkins
(74) *Attorney, Agent, or Firm* — Brian C. Trask

(57) ABSTRACT

A volatile substance delivery system includes a volatile substance container to contain a volatile substance, an optional absorbent and collapsible element disposed within the container to reduce presence of undesired air during manufacture of the device, an outlet to deliver a volume of the volatile substance from the volatile substance container toward an ambient environment, and a manual screw pump to reduce volume (or sometimes, just increase pressure) within the volatile substance container and promote the delivery of the volatile substance from the volatile substance container. A safety chamber is sometimes provided to resist unintended escape of volatile substance in liquid phase to the environment.

19 Claims, 10 Drawing Sheets

(56) References Cited

U.S. PATENT DOCUMENTS

2005/0185940 A1    8/2005   Joshi et al.
2006/0292304 A1    12/2006   Tisone

OTHER PUBLICATIONS

Copenheaver et al. "Written Opinion of the International Searching Authority" for PCT Application No. PCT/US2015/017837, dated Jun. 3, 2015, 8 pages.

\* cited by examiner

NONLEAKING VOLATILE SUBSTANCE DELIVERY SYSTEM

CROSS-REFERENCE TO RELATED APPLICATIONS

This application is a continuation-in-part of U.S. Utility application Ser. No. 15/396,759, titled "NO-DRIP VOLATILE SUBSTANCE DELIVERY SYSTEM", filed on Jan. 2, 2017, which is a continuation-in-part of U.S. Utility application Ser. No. 14/632,970, titled "VOLATILE SUBSTANCE DELIVERY SYSTEM", filed on Feb. 26, 2015, now U.S. Pat. No. 9,533,066, issued Jan. 3, 2017, which claims the benefit of U.S. Provisional Application No. 61/944,698, titled "ON DEMAND FRAGRANCE DELIVERY SYSTEM", filed on Feb. 26, 2014, and the continuation-in-part U.S. Utility application Ser. No. 15/396,759 is a continuation-in-part of U.S. Utility application Ser. No. 14/537,691, titled "VOLATILE SUBSTANCE DELIVERY SYSTEM", filed on Monday, Nov. 10, 2014, now U.S. Pat. No. 9,623,135, issued Apr. 18, 2017, which claims the benefit of U.S. Provisional Application No. 61/902,031, titled "FRAGRANCE DELIVERY SYSTEM", filed on Nov. 8, 2013, all of which are incorporated by reference herein in their entirety.

BACKGROUND

Conventional fragrance delivery systems use wicking to transfer the fragrance from a reservoir to a point of release from the device. However, wicking systems are inherently subject to many environmental conditions. This impacts the ability of the fragrance delivery system to control the release of the fragrance into the ambient environment. Without the ability to control the release of the fragrance, top notes typically evaporate first, followed by middle notes and then base notes (based on different volatility levels). In this way, conventional wicking systems over time often fail to provide full fragrances with the full range of combined notes.

SUMMARY

Embodiments of a system are described. In one embodiment, the system is a volatile substance delivery system. An embodiment of the volatile substance delivery system includes a volatile substance container, an outlet, and a manual screw pump. The volatile substance container contains an initial charge of the volatile substance. In certain embodiments, the volatile substance chamber is substantially free of gas that can expand and promote leaking of volatile substance from the chamber. In certain embodiments, the volatile substance container may be at least substantially filled with an absorbent collapsible material, like a sponge, and the volatile fluid is distributed throughout the absorbent material as an aid to displace gas from the chamber during manufacture. The outlet delivers a volume of the volatile substance from the volatile substance container to an ambient environment. It is preferred to provide a valve at the outlet to resist undesired escape of fluid from the volatile substance chamber.

Sometimes, a safety chamber is provided to resist delivery of liquid volatile substance to the environment. A preferred safety chamber is sized to confine the entire initial charge volume of the volatile substance container. The manual screw pump increases pressure within the volatile substance container and promotes the delivery of the volatile substance from the volatile substance container to the safety chamber. A preferred safety chamber is structure to resist escape of volatile substance in liquid phase to the environment.

An absorbent material may be disposed in the safety chamber to promote transport of volatile liquid toward an emanator. A preferred emanator allows evaporation of volatile substance from its outer surface to the local environment, but resists passage of volatile substance in liquid phase. Desirably, an inside surface of an emanator is maintained in a wetted state during the life of a volatile fluid dispensing device, to maintain a steady level of volatile fluid that is broadcast into the local environment. An absorbent material may be configured to facilitate maintenance of a steadily-wetted inside emanator surface. A workable absorbent material can provide capillary, wicking, or other mechanisms of fluid transport. Certain embodiments may include a liquid-tight safety chamber, with an emanator that allows evaporation of volatile fluid into the local ambient atmosphere, but resists flow of liquid to the environment.

Other embodiments of the system are also described and will be apprehended by one of ordinary skill. One or more element may be extracted from any of the disclosed embodiments, and combined to form an alternative embodiment within the spirit and scope of the instant invention.

Embodiments of a method to dispense a volatile substance to the environment are also described. In one embodiment, a method for operating a volatile substance delivery system includes twisting a manual screw pump. The method also includes compressing fluid within a volatile substance container in response to twisting the manual screw pump. The volatile substance container typically initially contains a volatile substance. In certain embodiments, the volatile substance is absorbed by, and distributed throughout, an absorbent material. A workable absorbent material includes a sponge, such as a commercially available cellulose sponge. When present, it is desirable for the absorbent material to fill the initial volume of the volatile substance container and to be saturated with the volatile substance. Sometimes, an absorbent element may be disposed in the safety chamber. The method also includes delivering a volume of the volatile substance from an outlet of the volatile substance container to an ambient environment in response to compressing the fluid within the volatile substance container. Sometimes, the method may include compressing and collapsing an absorbent material disposed inside the volatile substance container in response to twisting the manual screw pump. Other embodiments of the method are also described.

Embodiments of a method to manufacture a dispensing device for a volatile substance are also disclosed. One such method includes disposing an absorbent material inside a chamber to hold a volatile substance. In some cases, the absorbent material is structured and arranged to absorb volatile fluid as that fluid is loaded into the volatile substance chamber, and consequently, displace at least substantially all gas to fill an initial volume of the chamber. Subsequent to absorbing the volatile fluid, the absorbent material may be collapsed by action of a user to release volatile fluid to the environment. Fluid may be loaded into the absorbent element by way of injection, suction, convection, capillary attraction, or any other workable fluid transfer mechanism.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
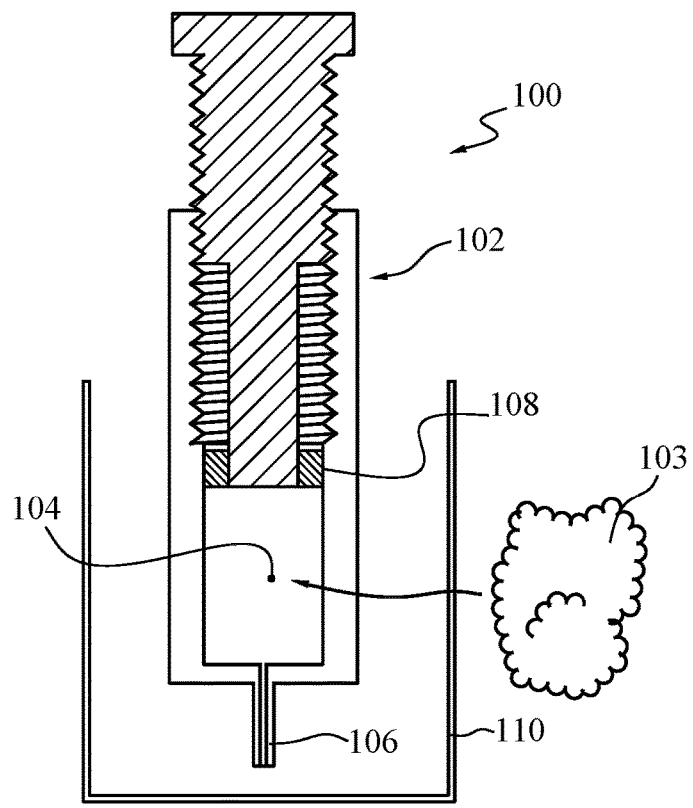
FIG. 1 illustrates one embodiment of a sealed manual fragrance delivery system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments facilitate on-demand delivery of a volatile substance. In general, the volatile substance refers to any fluid which is volatile such that it diffuses, evaporates, or otherwise changes in characteristics over time in certain environments. In some embodiments, the volatile substance may be a fragrance. Other embodiments may utilize other types of volatile substances. References to embodiments which utilize a fragrance are set forth as examples, but are not limiting to embodiments of the delivery system, which may deliver any of a variety of volatile substances.

The on-demand delivery of a fragrance or other volatile substance may be used to create an expected ambiance or environment for a user. For example, a user may utilize fragrance to optimize the user's sleeping environment and to enhance the user's bedtime routine. As another example, a user may utilize fragrance to enhance the user's vehicle environment and driving routine. Examples of other activities that may benefit from the use of fragrances include, but are not limited to, sleeping, studying, working, eating, and watching television.

In contrast to conventional wicking systems, certain embodiments described herein implement drop delivery systems. Drop delivery systems may be controlled more easily than conventional systems. Also, drop delivery systems can maintain a full or broader range of notes over a longer period of time, if the fragrance is not subjected to evaporation or other degrading environmental conditions. This allows each drop of the fragrance to deliver a mix of top, middle, and base notes throughout the operating lifecycle of a fragrance volume within a fragrance delivery system.

Embodiments of a volatile substance delivery system incorporate a volatile substance container to contain the volatile substance. The system also includes an outlet to deliver a volume of the volatile substance from the volatile substance container to an ambient environment. The outlet may be directly from the volatile substance container or, in other embodiments, from a downstream container or channel. The system also includes a manual screw pump to increase pressure within the volatile substance container and promote the delivery of the volatile substance from the volatile substance container. In further embodiments, the delivery system may include a combination of one or more additional components such as an emanator, a fan, a heat source for heating air, a heat source for heating the fragrance, and so forth. Other embodiments may include additional components.

A primary advantage of some embodiments described herein includes the ability to deliver the full depth of the fragrance, as opposed to just the high notes. In some embodiments, the system provides an immediate volume of fragrance that is then distributed into the ambient environment, to optimize an environment for a given activity. The volume of fragrance delivered is not subject to environmental conditions.

FIG. 1 illustrates one embodiment of a sealed manual fragrance delivery system 100. The illustrated fragrance delivery system 100 includes a manual screw pump 102, a fragrance container 104, an outlet 106, a piston plunger 108, and an emanator 110. Although the illustrated fragrance delivery system 100 includes certain components to achieve specific functionality, other embodiments of the pressurized chamber fragrance delivery system 100 may include fewer or more components to achieve similar or different functionality.

For one non-limiting example, an absorbent element 103 may be disposed inside the fragrance container 104. A workable absorbing element 103 includes a sponge, such as a commercially available cellulose sponge. When such an absorbing element 103 is present, it is desirable for the element 103 to have a configuration to at least substantially fill the initial volume of the fragrance container 104 when saturated with fragrance. A preferred absorbent element 103 soaks up fragrance, or other volatile substance, and is collapsible to permit release of the volatile substance into the ambient environment. In that case, fragrance may be loaded into the device 100 to displace substantially all air in the container 104 such that the saturated absorbing element 103 occupies the entire initial volume. The resulting device 100 is more resistant to undesired leaking of volatile substance due to significant increase in ambient temperature.

An exemplary case in which reduction of air in a volatile substance container 104 is helpful is during use of a fragrance dispensing embodiment in an automobile. The temperature inside an automobile in the summer time can easily reach over 150° F., particularly in the vicinity of the windshield. In contrast, a device 100 structured for use in that automobile may be assembled in an ambient temperature of about 70° F., or even less. As predicted by the Ideal Gas Law: PV=nRT, any air inside a device 100 can undergo a considerable pressure increase due to that 80+° F. change in temperature. A larger volume of air inherently causes a larger pressure increase (and/or the expansion of gas is larger compared to expansion of fluid under the same temperature change), and may displace a larger amount of volatile fluid. As a consequence, volatile fluid may undesirably be forced out from confinement in the container 104 by expansion of undesired air or other gas that is present in the volatile substance container. An optional absorbing element 103 may be structured to at least substantially reduce, if not completely eliminate, the amount of undesired air inside a device 100.

In one embodiment, the manual screw pump 102 is used to pressurize the fragrance container 104 containing the fragrance or other volatile substance. Any type of manual screw pump may be implemented. In some embodiments, the manual screw pump may have an exposed surface for engagement by a user's hand to manually turn the screw pump. In other embodiments, the manual screw pump may have a mechanical tool engagement surface for engagement of a mechanical tool such as a screwdriver or other hand tool to manually turn the screw pump.

In further embodiments, the manual screw pump may have either infinite or discrete turning positions. Infinite turning positions refer to the ability to rotate the manual screw pump 102 to any angle, without limitation to specific angles. In contrast, discrete turning positions refer to rotational steps, or increments, at which the manual screw pump 102 engages. For example, an embodiment of the manual screw pump 102 may have a fixed number of rotational positions (e.g., 2, 3, 5, 8, 10, 12, etc.) to which the piston plunger 108 will rotate within a single full rotation of the manual screw pump 102. Due to the helical arrangement of the screw threads, each fixed position corresponds to a unique fixed translational position of the piston plunger 108 relative to the outlet 106. Similarly, each fixed position also corresponds to a unique fixed volume of the fragrance container 104, and fixed incremental changes in that volume.

The piston plunger 108 is sealed to separate the threaded sidewalls from the portion of the fragrance container 104 that contains the fragrance or other volatile substance. The piston plunger 108 also seals the fragrance portion of the fragrance container 104 so that it can be pressurized, at least temporarily.

Pressurizing the fragrance container 104 causes the fragrance to be expelled from the fragrance container 104 through the outlet 106 to the emanator 110. The outlet may or may not include a valve or other control mechanism to control when the pressurized fragrance is released from the fragrance container 104. Once released and delivered to the emanator 110, the fragrance can evaporate into the ambient environment from the emanator 110. In further embodiments, additional mechanical and/or thermal assistance may be provided to accelerate evaporation of the fragrance from the emanator 110.

Some examples of emanator materials include, but are not limited to, porous polymers, simple cellular papers or films. In general, embodiments of the emanator 110 have a balance of absorption, wicking, and emanation properties that allow the emanator 110 to collect, distribute, and release the fragrance over time. In the illustrated embodiment, the emanator 110 at least partially or fully wraps around the fragrance container 104.

In some embodiments, the emanator 110 includes a porous material to collect, wick, and release the fragrance. The emanator 110 may or may not have its own structural integrity to maintain a specific shape while mounted within the fragrance delivery system. In some embodiments, the emanator material is applied to, or supported by, another support structure such as a cage or frame made of any suitable material.

Figure 2:
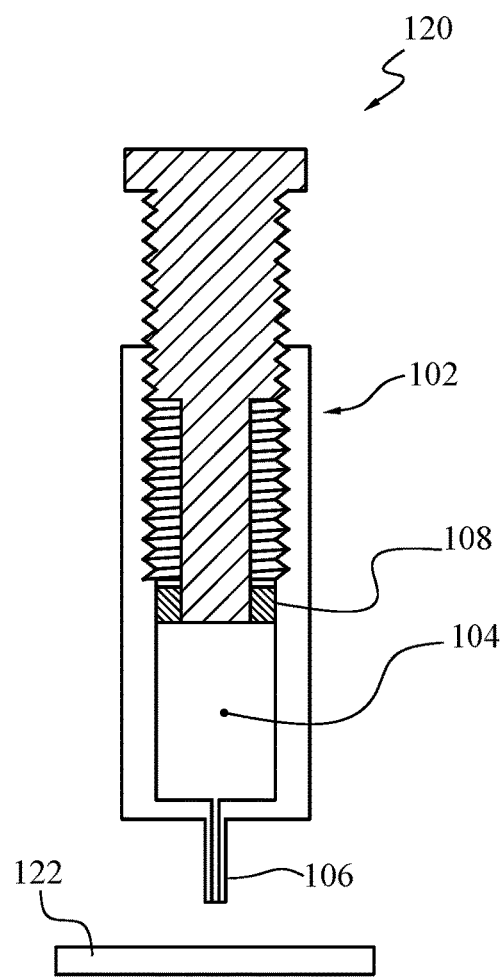
FIG. 2 illustrates another embodiment of a sealed manual fragrance delivery system which includes a separate emanator.

FIG. 2 illustrates another embodiment of a sealed manual fragrance delivery system 120 which includes a separate emanator 122. In contrast to the emanator 110 of FIG. 1, the emanator 122 of FIG. 2 is separated from the rest of the delivery system assembly. In other words, the emanator 122 does not wrap around parts of the fragrance container 104, and there is a distance of separation between the outlet 106 and the nearest surface of the emanator 122. In these embodiments, the delivery system 120 may be oriented to facilitate dropping the emitted fragrance from the outlet 106 under influence of gravity to the emanator 122.

In other embodiments, the outlet 106 includes a valve or other control mechanism to control how much of the pressurized fragrance is released from the fragrance container 104 at a single time. The valve or other control mechanism may allow pressure to build up within the fragrance container 102 until a threshold pressure has been reached, at which point the valve or other control mechanism may release a fixed volume of the fragrance is released. Alternatively, the valve or other control mechanism may release a variable volume of the fragrance until the pressure within the fragrance container 102 falls below a lower threshold pressure. In either case, the pressure of the fragrance may facilitate projecting or spraying the fragrance onto the emanator. In some embodiments, this pressurized transfer of the fragrance may facilitate a variety of orientations of the delivery system 102, instead of relying solely on gravity fed transfer.

Figure 3:
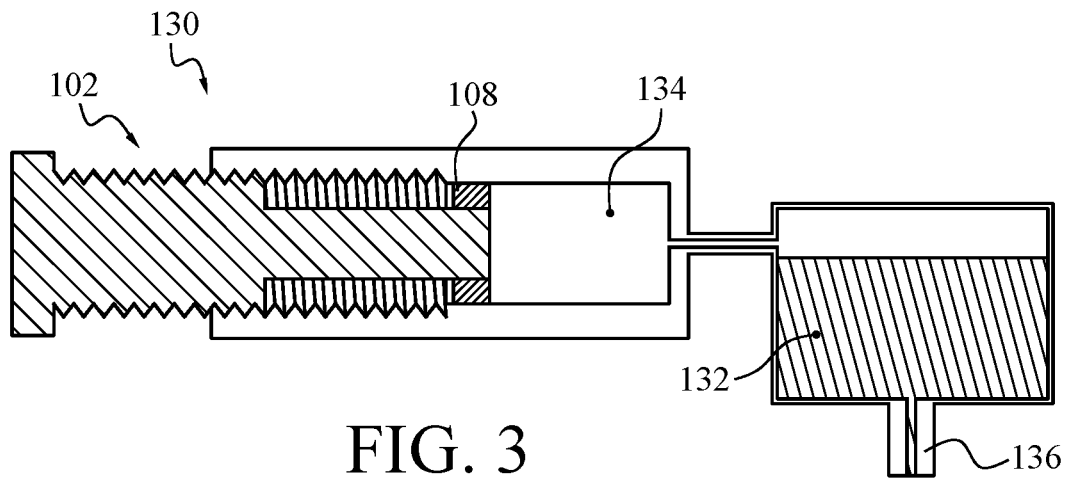
FIG. 3 illustrates another embodiment of a sealed manual fragrance delivery system which includes a separate fragrance chamber.

FIG. 3 illustrates another embodiment of a sealed manual fragrance delivery system 130 which includes a separate fragrance container 132. The piston plunger 108 is used to pressurize an intermediate container 134 of inert gas or liquid, which transfers through a channel to the separate fragrance container 132. As the pressure in the intermediate container 134 is transferred to the separate fragrance container 132, the fragrance is emitted from the fragrance container 132 to an emanator (not shown) or directly into the ambient environment. If an emanator is used, the emanator may be wrapped around part of, or all of the separate fragrance container 132, or located remotely from the separate fragrance container 132.

In certain cases, it is desirable to minimize the quantity of gas in either of (or typically both), intermediate container 134 and fragrance container 132. For example, it is desirable to avoid air bubbles, or gas bubbles, which would inherently promote leaking from a dispenser of fragrance for use in an automobile due to a large ambient temperature increase. Sometimes, careful manufacturing steps may be taken to avoid the presence of undesired gas. In other cases, an absorbent element 103 may be disposed in one or more container, to absorb a fluid and facilitate displacement of gas from the container during manufacture of a dispensing device. The absorbed fluid can respectively be an intermediate fluid in container 134, and/or a fragrance in container 132.

In some embodiments, the delivery system 130 may include a valve or other control mechanism within the transfer channel between the intermediate container 134 and the separate fragrance container 132. The valve or other control mechanism may control the timing and/or volume and/or pressure of the transfer from the intermediate container 134 to the separate fragrance container 132.

Figure 4:
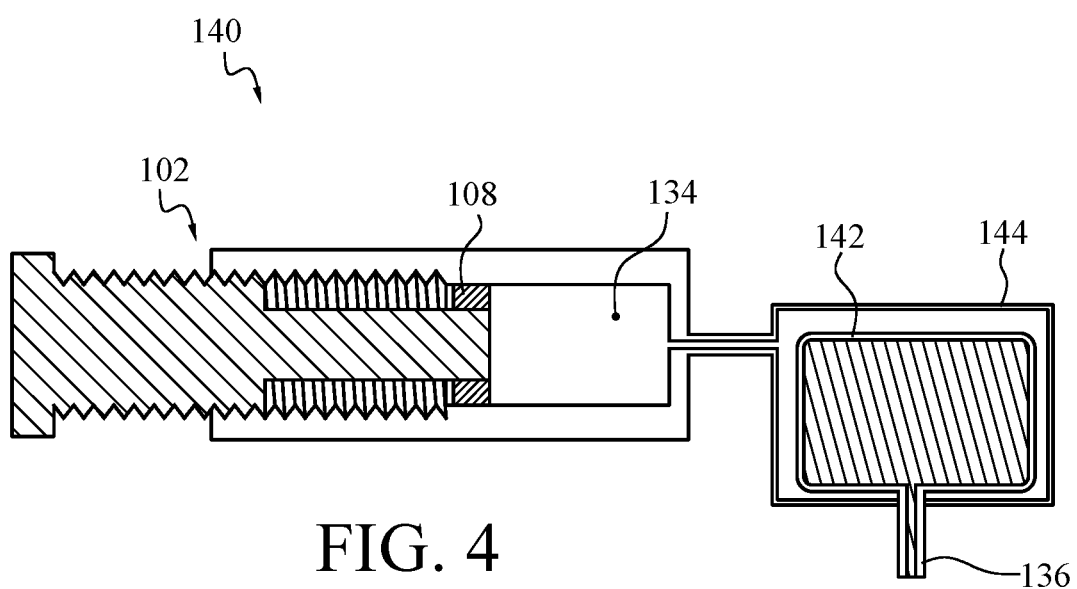
FIG. 4 illustrates another embodiment of a sealed manual fragrance delivery system which includes a separate flexible fragrance chamber.

FIG. 4 illustrates another embodiment of a sealed manual fragrance delivery system 140 which includes a separate flexible fragrance container 142. The separate flexible fragrance container 142 is disposed within a rigid outer housing 144. The piston plunger 108 is used to pressurize the intermediate container 134 of inert gas or liquid, which transfers through the channel to the outer housing 144. As the pressure in the outer housing 144 increases, the separate flexible fragrance container 142 is compressed and the fragrance is emitted to an emanator (not shown) or directly into the ambient environment.

As is the case for certain embodiments illustrated in FIGS. 1 and 2, it may be desirable to minimize the quantity of gas in either of (or typically both), intermediate container 134 and fragrance container 142. For example, it is desirable to avoid air bubbles, or gas bubbles, which would inherently promote leaking from a dispenser of fragrance for use in an automobile due to increased pressure in the gas caused by a large ambient temperature increase. Again, an absorbent element 103 (see FIG. 1) may be disposed in one or more container, to absorb a fluid and facilitate complete displacement of gas from the container during manufacture. The absorbed fluid can respectively be an intermediate fluid in container 134, or a fragrance in container 142. This gas thermal expansion principle applies regardless of the type of pump or plumbing arrangement that may be employed to dispense fragrance to a local environment. Expansion of only fluid due to a local ambient temperature increase causes a much smaller change in internal pressure, which can effectively be neglected.

Another way to consider the problem is: undesired gas in a fluid-holding chamber expands due to increase in local temperature, and the gas expands more than the fluid. Consequently, the expanded gas can displace a larger amount of fluid than would be displaced from a storage container by an equivalent temperature change.

Figure 5:
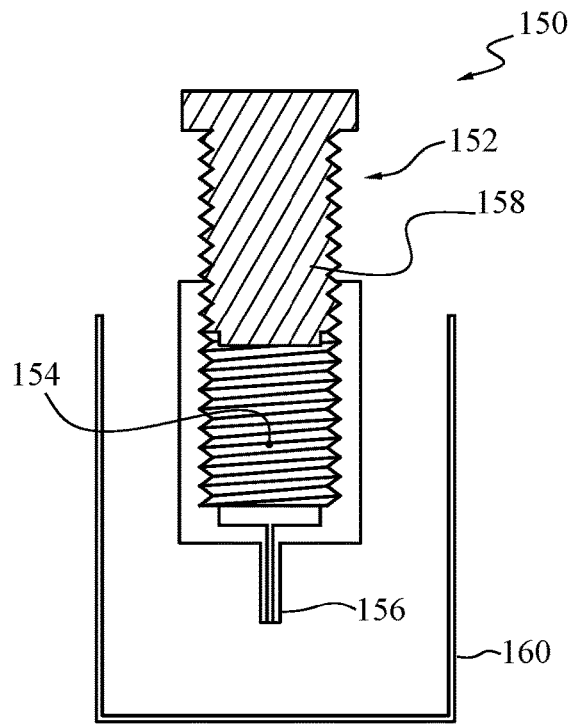
FIG. 5 illustrates another embodiment of a sealed manual fragrance delivery system which includes a manual screw pump with sealed threads.

FIG. 5 illustrates another embodiment of a sealed manual fragrance delivery system 150 which includes a manual screw pump 152 with sealed threads 158. The illustrated fragrance delivery system 150 includes the manual screw pump 152, a fragrance container 154, an outlet 156, the sealed threads 158, and an emanator 160. Although the illustrated fragrance delivery system 150 includes certain components to achieve specific functionality, other embodiments of the pressurized chamber fragrance delivery system 150 may include fewer or more components to achieve similar or different functionality.

The delivery system 150 of FIG. 5 is similar in many aspects to the delivery system 100 of FIG. 1, with the exception of the sealed threads 158 of FIG. 5. In the delivery system 100 of FIG. 1, the use of the sealed piston plunger 108 made it unnecessary to use sealed threads. However in the delivery system 150 of FIG. 5, the sealed threads 158. This alleviates the need for a separate seal.

As the threaded wall of the screw engages the corresponding threads on the interior sidewall of the fragrance container 154, the pressure within the fragrance container 154 increase and forces the fragrance to pass through the outlet 156 onto the emanator 160.

Figure 6:
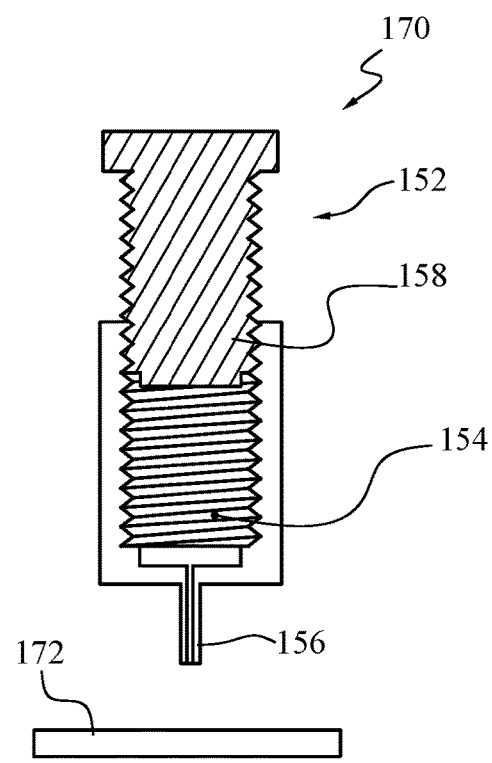
FIG. 6 illustrates another embodiment of a sealed manual fragrance delivery system which includes a separate emanator.

FIG. 6 illustrates another embodiment of a sealed manual fragrance delivery system 170 which includes a separate emanator 172. In contrast to the emanator 160 of FIG. 5, the emanator 172 of FIG. 6 is separated from the rest of the delivery system assembly, similar to the separate emanator 122 of FIG. 2.

Figure 7:
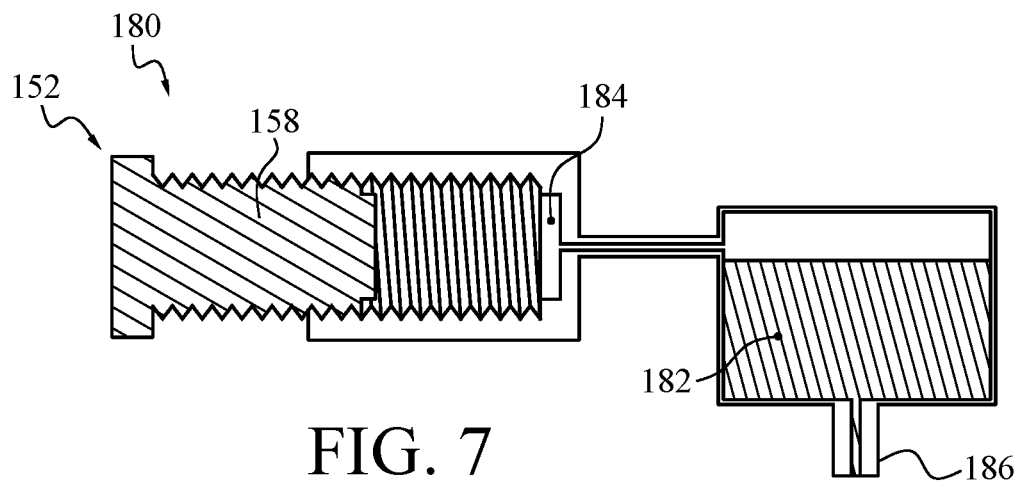
FIG. 7 illustrates another embodiment of a sealed manual fragrance delivery system which includes a manual screw pump with sealed threads and a separate fragrance chamber.

FIG. 7 illustrates another embodiment of a sealed manual fragrance delivery system 180 which includes a manual screw pump 152 with sealed threads 158 and a separate fragrance container 182. The manual screw pump 152 is used to pressurize an intermediate container 184 of inert gas or liquid, which transfers through a channel to the separate fragrance container 182. As the pressure in the intermediate container 184 is transferred to the separate fragrance container 182, the fragrance is emitted from the fragrance container 182 to an emanator (not shown) or directly into the ambient environment. If an emanator is used, the emanator may be wrapped around part of, or all of the separate fragrance container 182, or located remotely from the separate fragrance container 182.

Figure 8:
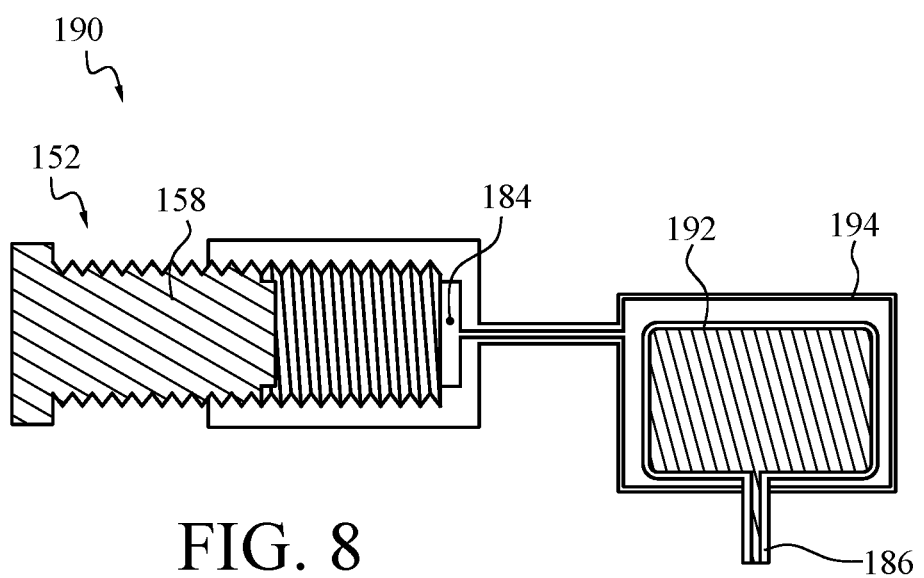
FIG. 8 illustrates another embodiment of a sealed manual fragrance delivery system which includes a manual screw pump with sealed threads and a separate flexible fragrance chamber.

FIG. 8 illustrates another embodiment of a sealed manual fragrance delivery system 190 which includes a manual screw pump 152 with sealed threads 158 and a separate flexible fragrance container 192. The separate flexible fragrance container 192 is disposed within a rigid outer housing 194. The manual screw pump 152 is used to pressurize the intermediate container 184 of inert gas or liquid, which transfers through the channel to the outer housing 194. As the pressure in the outer housing 194 increases, the separate flexible fragrance container 192 is compressed and the fragrance is emitted to an emanator (not shown) or directly into the ambient environment.

Figure 9:
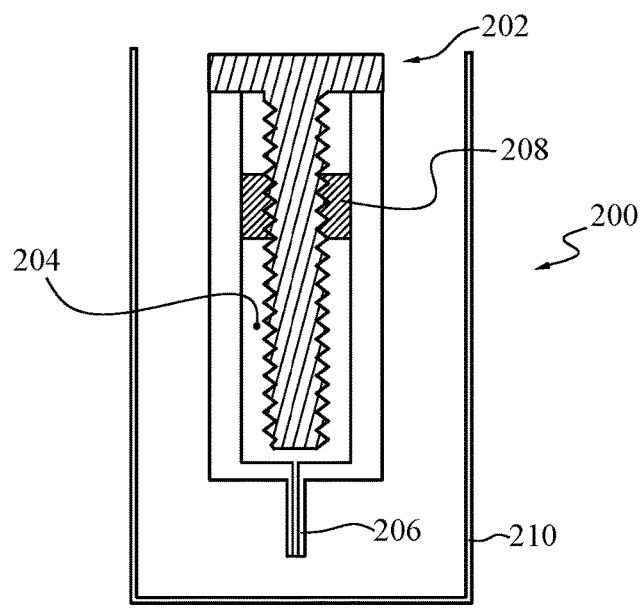
FIG. 9 illustrates another embodiment of a sealed manual fragrance delivery system which includes a sealed piston and a separate emanator.

FIG. 9 illustrates another embodiment of a sealed manual fragrance delivery system 200 which includes a sealed piston 208 and an emanator 210 enclosing the assembly. The illustrated fragrance delivery system 200 includes a manual screw pump 202, a fragrance container 204, an outlet 206, the sealed piston 208, and the emanator 210. Although the illustrated fragrance delivery system 200 includes certain components to achieve specific functionality, other embodiments of the pressurized chamber fragrance delivery system 200 may include fewer or more components to achieve similar or different functionality.

The delivery system 200 of FIG. 9 is similar in many aspects to the delivery system 100 of FIG. 1, with the exception of the location of the sealed piston plunger 208. In the delivery system 100 of FIG. 1, the sealed piston plunger 108 is located at an end of the threaded screw, which moves as a whole toward the outlet 106. In contrast, the threaded screw of FIG. 9 rotates, but does not move toward or away from the outlet 206. The sealed piston plunger 208 moves along the threaded screw as it is rotated, decreasing the volume between the sealed piston plunger 108 and the outlet 206. This alleviates the need for additional clearance at the head of the manual screw pump 202.

Figure 10:
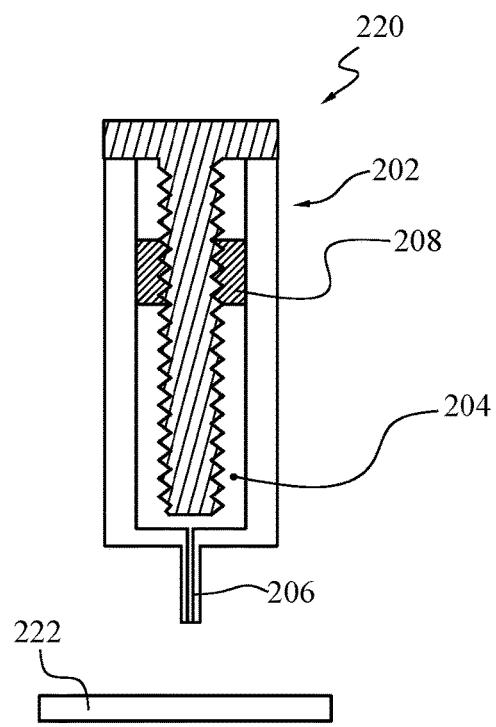
FIG. 10 illustrates another embodiment of a sealed manual fragrance delivery system which includes a sealed piston and an emanator enclosing the assembly.

FIG. 10 illustrates another embodiment of a sealed manual fragrance delivery system 220 which includes a sealed piston 208 and a separate emanator 222. In contrast to the emanator 210 of FIG. 9, the emanator 222 of FIG. 10 is separated from the rest of the delivery system assembly, similar to the separate emanator 122 of FIG. 2.

Figure 11:
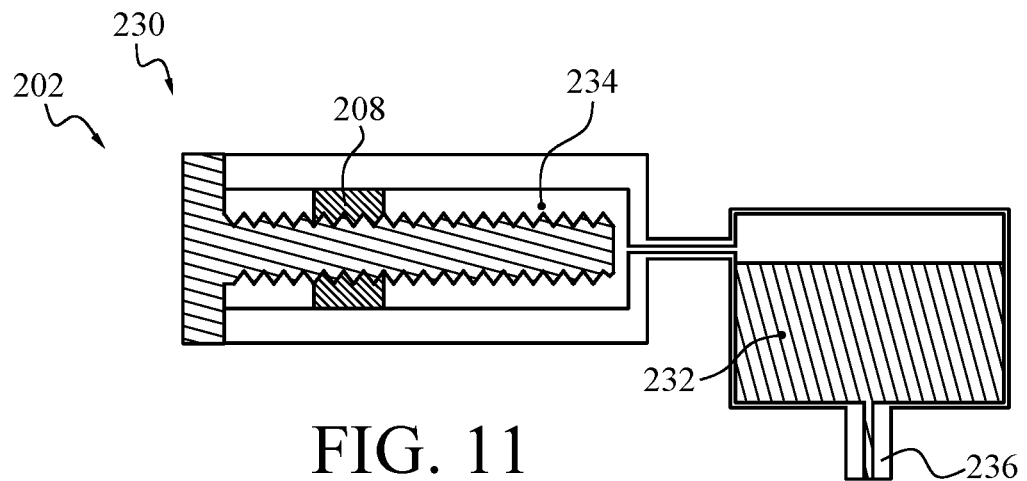
FIG. 11 illustrates another embodiment of a sealed manual fragrance delivery system which includes a sealed piston and a separate fragrance chamber.

FIG. 11 illustrates another embodiment of a sealed manual fragrance delivery system 230 which includes a sealed piston 208 and a separate fragrance container 232. The manual screw pump 202 is used to pressurize an intermediate container 234 of inert gas or liquid, which transfers through the channel to the separate fragrance container 232. As the pressure in the intermediate container 234 is transferred to the separate fragrance container 232, the fragrance is emitted from the fragrance container 232 to an emanator (not shown) or directly into the ambient environment. If an emanator is used, the emanator may be wrapped around part of, or all of the separate fragrance container 232, or located remotely from the separate fragrance container 232.

Figure 12:
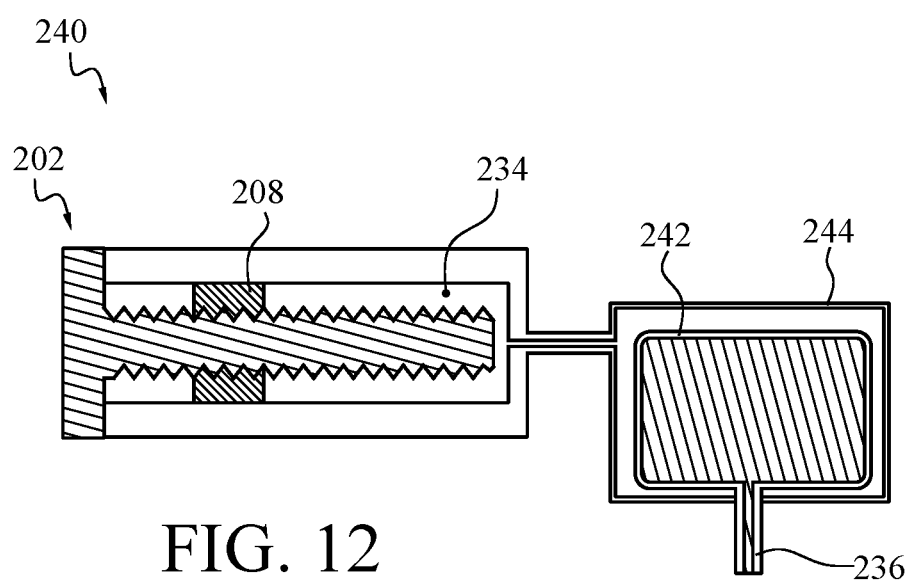
FIG. 12 illustrates another embodiment of a sealed manual fragrance delivery system which includes a sealed piston and a separate flexible fragrance chamber.

FIG. 12 illustrates another embodiment of a sealed manual fragrance delivery system 240 which includes a sealed piston 208 and a separate flexible fragrance container 242. The separate flexible fragrance container 242 is disposed within a rigid outer housing 244. The manual screw pump 202 is used to pressurize the intermediate container 234 of inert gas or liquid, which transfers through the channel to the outer housing 244. As the pressure in the outer housing 244 increases, the separate flexible fragrance container 242 is compressed and the fragrance is emitted to an emanator (not shown) or directly into the ambient environment.

Figure 13:
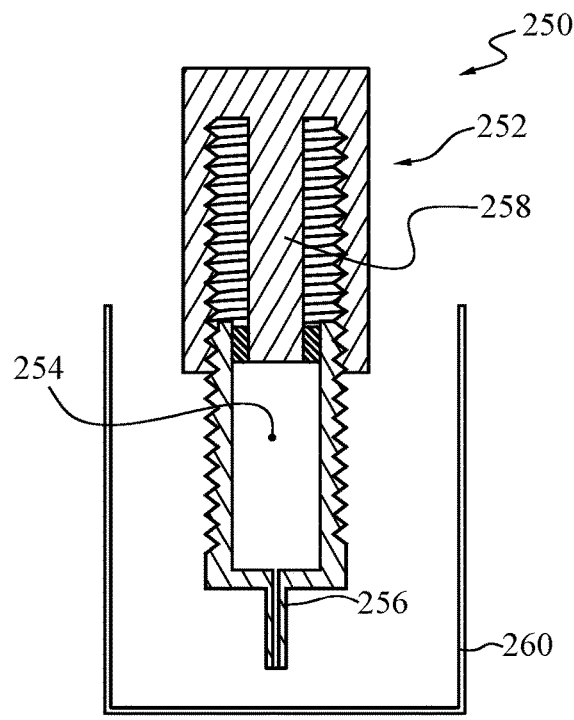
FIG. 13 illustrates another embodiment of a sealed manual fragrance delivery system which includes external threads outside of a piston chamber.

FIG. 13 illustrates another embodiment of a sealed manual fragrance delivery system 250 which includes external threads outside of a fragrance container 254. The illustrated fragrance delivery system 250 includes a manual screw pump 252, a fragrance container 254, an outlet 256, a sealed piston 258, and an emanator 260. Although the illustrated fragrance delivery system 250 includes certain components to achieve specific functionality, other embodiments of the pressurized chamber fragrance delivery system 250 may include fewer or more components to achieve similar or different functionality.

The delivery system 250 of FIG. 9 is similar in many aspects to the delivery system 100 of FIG. 1, with the exception of the location of the threads for the manual screw pump 252. In the delivery system 100 of FIG. 1, the threads are located inside the same cavity as the fragrance container 104. Specifically, the threads are located on the outside wall of the central post, and corresponding threads are located on the inner sidewall of the cavity as the fragrance container 104. In contrast, the threads for the embodiment of FIG. 13 are located outside the cavity that contains the fragrance. Instead, the threads are located on wall surfaces other than on the post. This may allow the piston plunger 258 to seal between two smooth walls.

Figure 14:
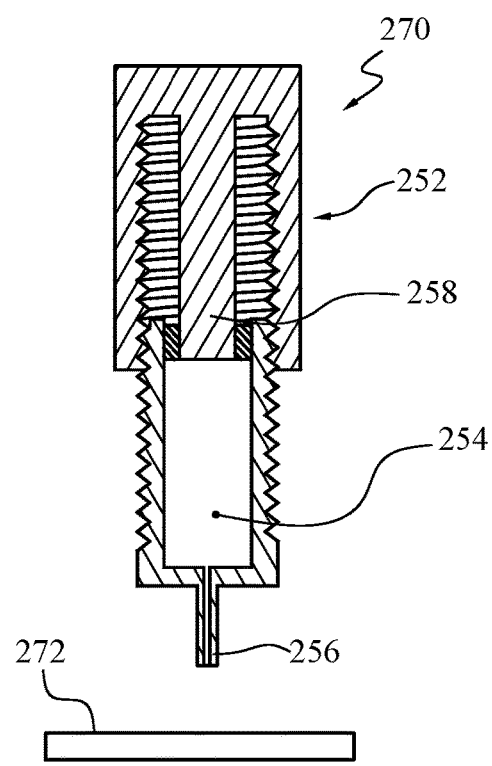
FIG. 14 illustrates another embodiment of a sealed manual fragrance delivery system which includes external threads outside of a piston chamber and a separate emanator.

FIG. 14 illustrates another embodiment of a sealed manual fragrance delivery system 170 which includes external threads outside of a fragrance container 254 and a separate emanator 272. In contrast to the emanator 260 of FIG. 13, the emanator 272 of FIG. 14 is separated from the rest of the delivery system assembly, similar to the separate emanator 122 of FIG. 2.

Figure 15:
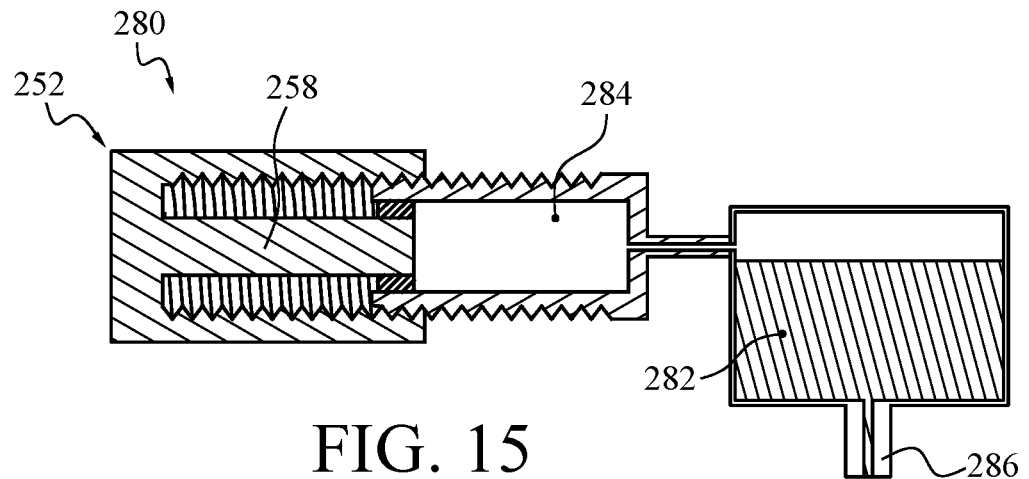
FIG. 15 illustrates another embodiment of a sealed manual fragrance delivery system which includes external threads outside of a piston chamber and a separate fragrance chamber.

FIG. 15 illustrates another embodiment of a sealed manual fragrance delivery system 280 which includes external threads and a separate fragrance container 282. The manual screw pump 252 is used to pressurize an intermediate container 284 of inert gas or liquid, which transfers through a channel to the separate fragrance container 282. As the pressure in the intermediate container 284 is transferred to the separate fragrance container 282, the fragrance is emitted from the fragrance container 282 to an emanator (not shown) or directly into the ambient environment. If an emanator is used, the emanator may be wrapped around part of all of the separate fragrance container 282, or located remotely from the separate fragrance container 282.

Figure 16:
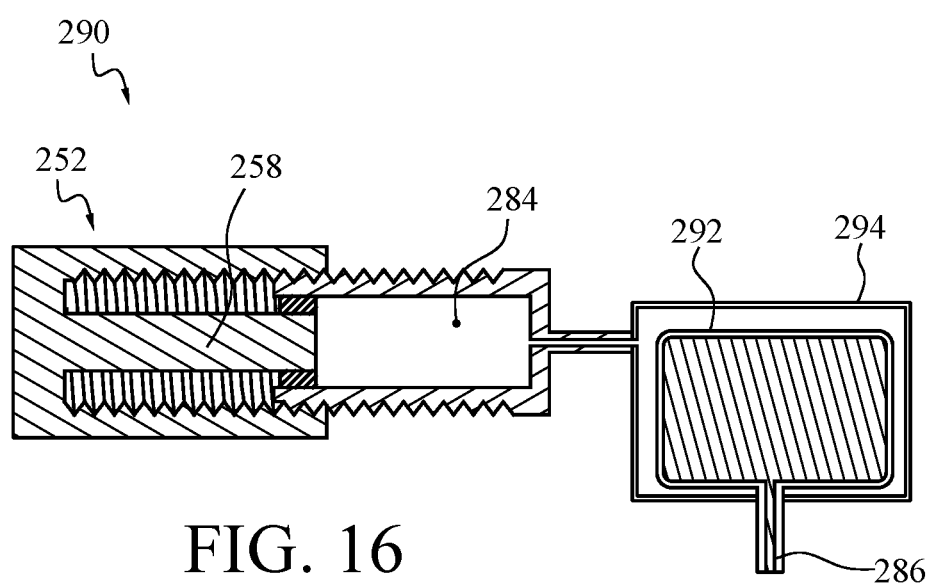
FIG. 16 illustrates another embodiment of a sealed manual fragrance delivery system which includes external threads outside of a piston chamber and a separate flexible fragrance chamber.

FIG. 16 illustrates another embodiment of a sealed manual fragrance delivery system 290 which includes external threads and a separate flexible fragrance container 292. The separate flexible fragrance container 292 is disposed within a rigid outer housing 294. The manual screw pump 252 is used to pressurize the intermediate container 284 of inert gas or liquid, which transfers through the channel to the outer housing 294. As the pressure in the outer housing 294 increases, the separate flexible fragrance container 292 is compressed and the fragrance is emitted to an emanator (not shown) or directly into the ambient environment.

The invention may be embodied to provide a method for manufacturing a no-drip dispenser of volatile fluid. One such method includes providing a volatile fluid delivery device with a volatile fluid chamber to hold a volatile fluid and a manual screw pump operable to displace volatile fluid from the volatile fluid chamber. A collapsible and absorbent element 103 may be disposed in the volatile substance container to facilitate removal of air from the device when loading the volatile fluid into the device. Desirably, the absorbent element 103 is structured such that an initial volume of the volatile substance container is substantially occupied by the absorbent element when saturated by a volatile substance to displace undesired air in the volatile substance container.

By initial volume, it is contemplated that the chamber volume may be reduced during operation of the dispensing device. In general, the absorbent element 103 is structured to be collapsible under operation of the screw pump to discharge volatile fluid from the volatile fluid chamber. The method includes charging the volatile fluid chamber with a quantity of volatile fluid effective to displace substantially all air in the initial volume of the volatile fluid chamber. Fluid may be loaded into the absorbent element by way of injection, suction, convection, capillary attraction, or any other workable fluid transfer mechanism.

Figure 17:
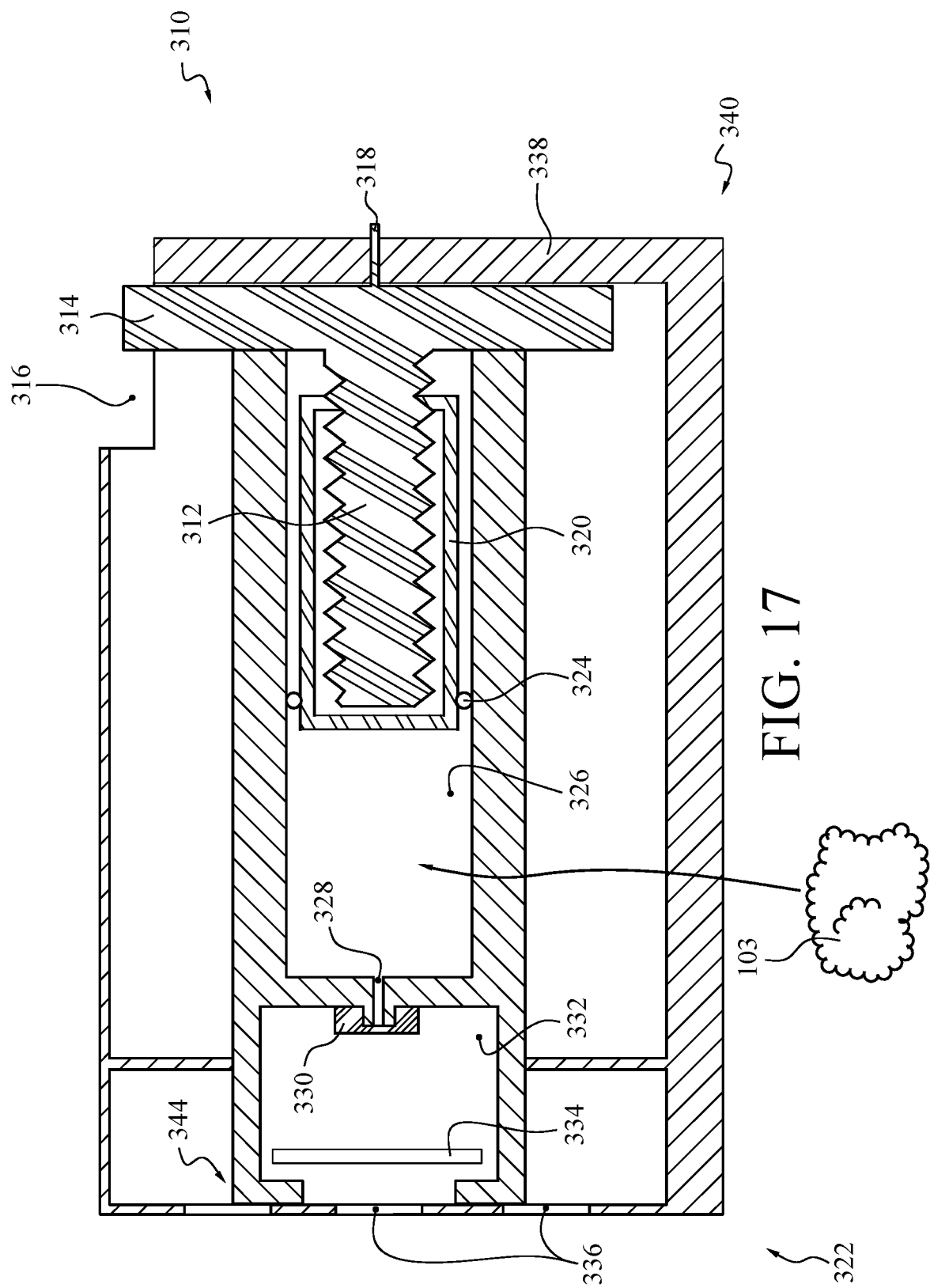
FIG. 17 illustrates another embodiment of a sealed manual fragrance delivery system which includes a sealed piston to change the volume of a fragrance chamber.

FIG. 17 illustrates another embodiment of a manual fragrance delivery system 310 which includes a threaded actuator shaft 312 that is rotated by way of a user interacting with actuator knob 314. Threaded shaft 312 engages a threaded wall at the proximal end of the piston plunger 320. Window 316 provides access for a user's finger to engage actuator knob 314. Knob 314 may be rotated about axle 318 to cause a compression in the shaft 312 and drive piston plunger 320 toward the discharge end, generally indicated at 322. Cylindrical piston plunger 320 is sealed on its distal end, as indicated at O-ring 324, to urge volatile fluid contained inside cooperating plunger chamber 326 (AKA volatile fluid chamber) toward aperture 328 for discharge into the local environment. It is currently preferred to structure device 310 to permit a user to see contents of the chamber 326 to evaluate remaining device life.

Certain embodiments may include a valve member 330 to resist unintended discharge of fluid. One operable valve member 330 establishes a threshold pressure required before fluid is permitted to flow through the discharge aperture 328. A workable valve 330 resists accidental draining of the plunger chamber 326 by way of e.g., gravity, or wicking. A preferred valve operates to "burp" out a drop, or so, then resist further liquid discharge until the critical pressure is again exceeded.

Further, a safety chamber or reservoir 322 may be provided to hold a quantity of fluid that is improperly, or accidentally, discharged. For example, a child may play with the discharge mechanism 314 and discharge a significant portion of volatile liquid fluid. Safety reservoir 332 provides a catch basin to hold the fluid, rather than permit the liquid to leak onto and damage e.g., upholstery or carpeting in an automobile. A safety reservoir 332 within contemplation may be sized to hold the entire initial (or as-manufactured) contents of volatile liquid fluid chamber 326. The initial liquid volume confined in chamber 326 may be characterized as a charge volume. An emanator 334 is typically provided to facilitate distribution and evaporation of the volatile liquid fluid in chamber 332 over a large area. Volatile fluid that evaporates from the exposed surface of emanator 334 is then dispensed to the local environment through one or more apertures 336.

It is preferred for threaded shaft 312 to be left-hand threaded. In that case, a user can twist or displace the actuator knob 314 in a clock-wise direction to dispense volatile substance from the volatile substance chamber. As indicated above, the threaded shaft 312 is placed into compression to urge motion of plunger 320. The end portion 338 of housing 340 forms a fixed restraint against which the actuator knob 314 presses to urge motion of the plunger 320. The window 316 is formed in housing 340, and permits a user access to manipulate actuator knob 314. Foot 344 is engaged on discharge end 322, so as plunger 320 moves distally, a volume in chamber 326 can be reduced to discharge volatile fluid from the chamber 326. As is the case with certain other embodiments, sometimes an absorbent element 103 may be included in the volatile substance chamber 326 to facilitate removal of gasses from the chamber 326 during manufacture of a device 310. The absorbent element 103 collapses, as the volume of chamber 326 is reduced by displacement of plunger 320, to release volatile fluid for discharge through aperture 328 toward a local ambient environment.

Figure 18:
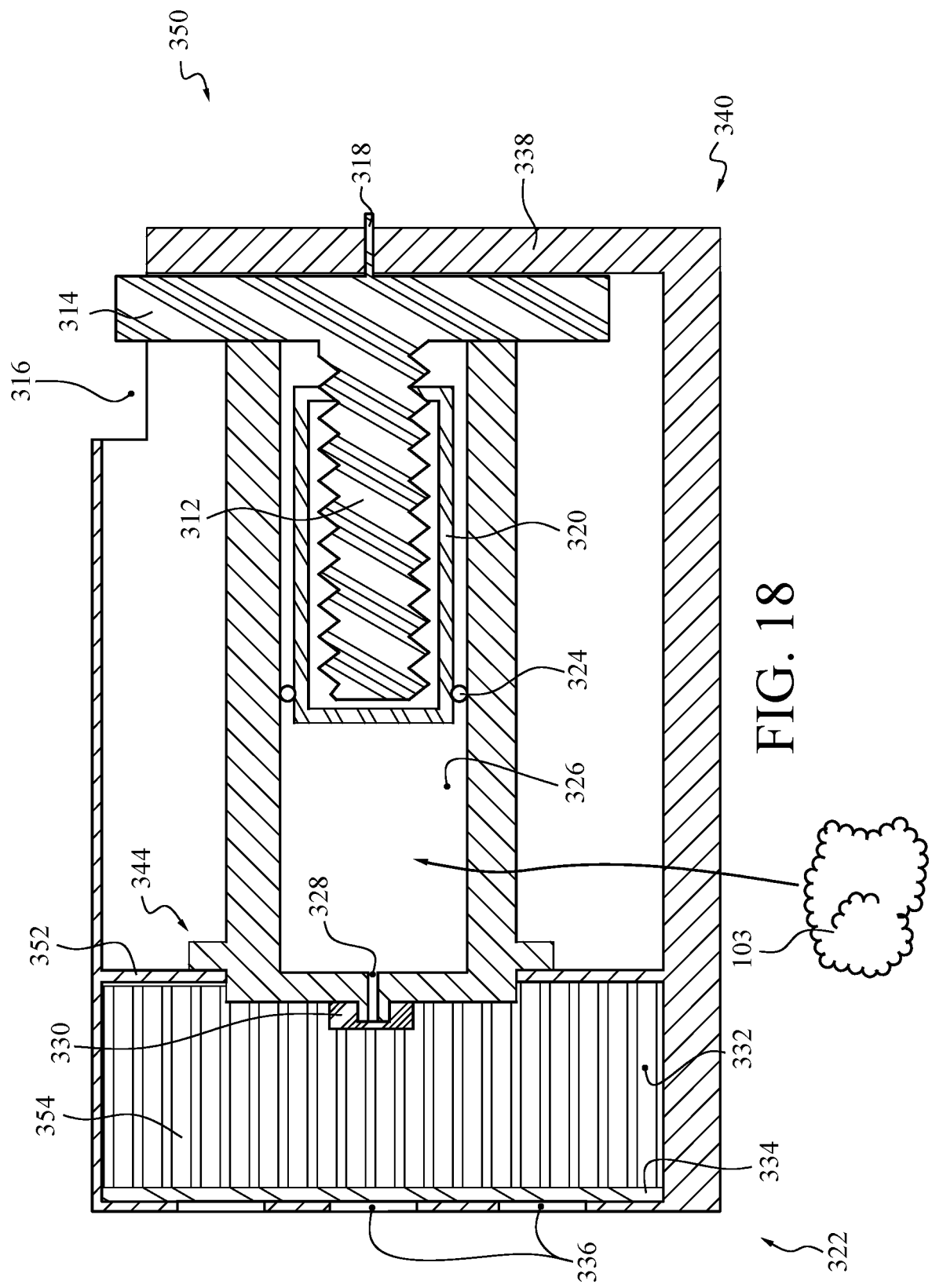
FIG. 18 is a side view in cross-section of an embodiment similar to that illustrated in FIG. 17.

The embodiment indicated generally at 350 in FIG. 18 is somewhat similar to embodiment 310 in FIG. 17. Artistic license has been taken with the structure illustrated in FIG. 18, but one of ordinary skill will appreciate how the device 350 may be constructed for assembly (for example, including a clam-shell housing, with subsequent bonding and assembly steps). One or more foot 344 engages cooperating structure of housing 340 to hold the hold chamber 326 in place during operation of actuator knob 314. As illustrated, feet 344 interfere with front wall 352 to resist axial motion of the chamber 326. An additional interference (not illustrated), or other restraint, may be provided to resist relative circumferential or rotational motion between chamber 326 and housing 340.

It is currently preferred to provide a fluid barrier at the rear end of safety reservoir 332. As illustrated, the distal end of chamber 326 forms a fluid-tight connection with wall 352. It is also preferred to arrange an emanator 334 as a cooperating front-side fluid-tight barrier for safety reservoir 332, to facilitate at least initial confinement of liquid discharged from chamber 326. For embodiments similar to 350, it is preferred for the emanator also to be resistant to liquid fluid flow, to confine liquid inside the safety chamber 332.

A workable emanator 334 in embodiment 350 includes a microporous membrane, such as heat-shrink material, that permits passage of fluid in vapor phase, but resists passage of fluid in liquid phase. Alternative workable liquid fluid-flow resisting emanator materials nonexclusively include various heat-shrinkable polymeric or nano-porous polymeric materials, (such as polyolefin heat-shrinking membrane), sheets or membranes of styrene-based or butadiene-based plastic, rubber, or rubber-like material, and mixtures there-of, thermoplastic urethane (TPU), or other material through which volatile fluid molecules may permeate or migrate for application to the local atmosphere, EPDM, gum rubber, cellulosic rubber, and other materials that absorb and emanate a fragrant volatile material, and the like.

Certain embodiments may not include the optional liquid fluid-flow resisting membrane element 334. An alternative to resist easy escape of liquid from safety chamber 332 includes an absorbent element 354 disposed to soak up liquid that has been discharged from chamber 326. A workable absorbent element 354 includes a sponge, or sponge-like element, such as a polymer or cellulose sponge, cotton ball, or wad of fibrous material, and the like. A sponge-like element 354 may be sufficient, on its own, to resist undesired direct discharge of liquid from the device 350 to the environment.

In some cases, it is desirable to include an absorbent element 354 as well as an emanator 334 that operates as a liquid fluid barrier. A preferred absorbent element 354 operates as a wicking element to transfer liquid fluid to, and distribute fluid over a significant portion of area of the emanator 334. Certain elements 354 may be configured to produce a capillary action on the liquid received from chamber 326, and thereby facilitate transfer of that liquid to the emanator 334. It is generally desirable to maintain the inside surface of the emanator in a wetted state, to produce a substantially constant application of scent to the local environment. Desirably, a significant portion (if not the entire inner surface) of the emanator is maintained in a wetted state to maintain a substantially constant humanly-perceived aroma over the working life of an emanator or device.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An apparatus, comprising:
   a volatile substance container to contain a charge volume of a volatile substance;
   a safety chamber sized to encompass at least the charge volume;
   an outlet of the volatile substance container to deliver a volume of the volatile substance from the volatile substance container to the safety chamber;
   an outlet of the safety chamber to permit discharge of volatile substance into the local environment; and
   a pump to increase pressure within the volatile substance container and promote discharge of the volatile substance from the volatile substance container, wherein:
   the pump is a manual screw pump comprising a threaded element and a piston plunger operably coupled to the threaded element.

2. The apparatus of claim 1, wherein the threaded element engages a threaded portion of the volatile substance container, and the piston plunger engages a non-threaded sidewall of the volatile substance container to create a movable seal between the piston plunger and the non-threaded sidewall of the volatile substance container.

3. The apparatus of claim 1, wherein the piston plunger engages a non-threaded sidewall of a plunger chamber disposed in a housing, wherein a window in the housing is configured and arranged to permit a user to operate an actuator knob to compress the threaded element and displace the plunger for discharge of volatile substance from the plunger chamber.

4. The apparatus according to claim 3, wherein the threaded element is left-hand threaded.

5. The apparatus of claim 1, further comprising a valve element disposed to resist unintended discharge of volatile substance through the outlet, the valve element being structured to establish a threshold pressure required before volatile substance is permitted to pass through the outlet.

6. The apparatus of claim 1, further comprising an emanator associated with a discharge from the safety chamber to the local environment, the emanator operable to release volatile substance in vapor form to the local environment.

7. The apparatus according to claim 6, wherein the emanator is structured to resist escape of liquid from the safety chamber.

8. The apparatus according to claim 1, further comprising an absorbent element disposed inside the safety chamber, the absorbent element disposed to uptake any liquid discharged from the volatile substance container.

9. The apparatus according to claim 8, further comprising an emanator associated with a discharge from the safety chamber to the local environment, the emanator operable to release volatile substance in vapor form to the local environment.

10. The apparatus according to claim 9, wherein the emanator is structured to resist escape of liquid from the safety chamber.

11. The apparatus according to claim 1, wherein the safety chamber is structured to permit release only of volatile substance in vapor phase into the local environment.

12. The apparatus according to claim 9, wherein the absorbent element is configured and arranged to transport liquid toward the emanator.

13. The apparatus according to claim 9, wherein the absorbent element is configured and arranged to maintain a portion of the emanator in a wetted state during the operating life of the apparatus.

14. The apparatus according to claim 9, wherein the absorbent element is configured and arranged to maintain substantially the entire inner surface of the emanator in a wetted state during the operating life of the apparatus.

15. A method for manufacturing a volatile substance delivery system, the method comprising:
   providing a volatile fluid delivery device comprising a volatile fluid chamber to hold a volatile fluid and a manual screw pump operable to displace volatile fluid from the volatile fluid chamber;
   coupling the volatile fluid chamber to a safety chamber, the safety chamber being sized to hold an entire initial charge volume of the volatile substance container; and
   charging the volatile fluid chamber with the initial charge volume of volatile fluid.

16. The method according to claim 15, further comprising installing an emanator in association with all outlets from the safety chamber, the emanator being structured to resist escape of fluid from the safety chamber.

17. The method according to claim 15, further comprising installing an absorbent element inside the safety chamber.

18. The method according to claim 17, wherein the absorbent element is disposed and arranged to transport liquid from the volatile fluid chamber toward an emanator, the emanator being structured to resist escape of fluid from the safety chamber.

19. A method for operating a volatile fluid delivery system, the method comprising:
   twisting a manual screw pump that is coupled to a volatile liquid chamber holding an initial charge volume of volatile liquid;

transferring a dose of volatile liquid to a safety chamber responsive to the twisting step, the safety chamber being sized to hold at least the entire initial charge volume; and delivering volatile fluid only in vapor phase from the safety chamber to a local environment.

\* \* \* \* \*